(12) United States Patent
Ryan et al.

(10) Patent No.: US 6,972,018 B2
(45) Date of Patent: Dec. 6, 2005

(54) APPARATUS AND METHOD FOR TRANSCERVICAL STERILIZATION BY APPLICATION OF ULTRASOUND

(75) Inventors: Thomas P. Ryan, Flemington, NJ (US); John S. Crombie, East Hanover, NJ (US)

(73) Assignee: Gynecare a division of Ethicon, Inc., Somerville, NJ (US)

( * ) Notice: Subject to any disclaimer, the term of this patent is extended or adjusted under 35 U.S.C. 154(b) by 314 days.

(21) Appl. No.: 10/185,417

(22) Filed: Jun. 28, 2002

(65) Prior Publication Data

US 2004/0002700 A1 Jan. 1, 2004

(51) Int. Cl.[7] .............................................. A61B 18/18

(52) U.S. Cl. ........................... 606/50; 606/40; 606/41; 606/135

(58) Field of Search ...... 606/41–52, 135; 607/48–103, 607/152; 601/2, 3

(56) References Cited

U.S. PATENT DOCUMENTS

| | | | |
|---|---|---|---|
| 5,620,479 A | 4/1997 | Diederich | |
| 5,733,315 A | 3/1998 | Burdette et al. | |
| 6,011,995 A | * 1/2000 | Guglielmi et al. | ............ 607/99 |
| 6,066,139 A | 5/2000 | Ryan et al. | |
| 6,206,831 B1 | 3/2001 | Suorsa et al. | |

FOREIGN PATENT DOCUMENTS

| | | |
|---|---|---|
| EP | 0 634 188 A1 | 1/1995 |
| EP | 1 125 548 A1 | 8/2001 |

OTHER PUBLICATIONS

Penny L. Ross, et al., "Transcatheter Tubal Sterilization in Rabbits Technique and Results", Investigative Radiology, vol. 29, No. 5, J.B. Lippincott Company, (1994), pp. 570-573.

Thomas P. Ryan, "Historical Perspective on Procedures to Ligate the Fallopian Tube for Sterilization", Critical Reviews, vol. CR75, Ethicon, Somerville, NJ, pp. 195-230.

B.H. Sheares, "Sterilization of Woman by Intra-Uterine Electro-Caulery of the Uterine Comu", The Department of Obstetrics and Gynaecology, University of Malaya, pp. 419-427.

Jack Shuber, "Transcervical Sterilization with Use of Methyl 2-Cyanoacrylate and a Newer Delivery System (the FEMCEPT Deivce)", Forty-Forth Annual Meeting of the Society of Obstetricians and Gynaecologists of Canada, Vancouver, British Columbia, Canada, (1988), pp. 887-889.

* cited by examiner

Primary Examiner—Rosiland Rollins (57) ABSTRACT

An apparatus for sterilizing a female patient in a transcervical procedure comprises an elongated catheter with a piezoelectric ultrasound transducer at its distal end. The catheter is inserted transcervically into the uterus and guided to the intramural region of a fallopian tube. The transducer is inserted into the intramural region in direct contact with the surrounding tissue. The transducer produces a radially dispersing acoustical wave front, heating the adjacent tissue and forming a thermal lesion therein. A fibrous tissue forms during the healing process, sealing the fallopian tube. An embodiment of the apparatus includes a movable thermal sensor for monitoring the tissue temperature at multiple locations along the lesion. Another embodiment of the apparatus includes a spring that centers the distal end of the catheter at the opening of the fallopian tube and provides a tactile means to determine that the catheter and transducer have been correctly positioned.

20 Claims, 8 Drawing Sheets

APPARATUS AND METHOD FOR TRANSCERVICAL STERILIZATION BY APPLICATION OF ULTRASOUND

FIELD OF THE INVENTION

The present invention relates to apparatus and methods for transcervical sterilization of a female patient and, more particularly, to transcervical methods and apparatus utilizing a piezoelectric transducer to create thermal lesions in fallopian tubes.

BACKGROUND OF THE INVENTION

Surgical procedures used to sterilize women for the prevention of pregnancy commonly involve coagulation of fallopian tubes by the electrosurgical generation of heat. The fallopian tubes typically are exposed by abdominal incisions so that the surgeon may observe the extent of coagulation as the operation progresses.

Various methods utilize the application of radiofrequency (RF) electrical current to heat the tissue to the temperatures at which it coagulates. As discussed, for example, in U.S. Pat. No. 6,066,139, these techniques sometimes fail to provide the necessary certainty of a successful sterilization, whether because of difficulties in controlling the application of the electrical energy, uncertainty in placement of the electrical probe, or for other reasons.

Various devices have been developed utilizing ultrasound generated by piezoelectric transducers to ablate tissues by heating. For instance, U.S. Pat. No. 5,620,479 discloses an ultrasound applicator comprising a plurality of piezoelectric transducers on a "semi-flexible" central tube for insertion in a body lumen or directly into tissue. A sealant coating is provided around the transducers, while an air cooling system is provided to control treatment temperature. Thermal sensors are embedded in the sealant.

U.S. Pat. No. 5,733,315 relates to the thermal ablation of prostate tissue with the use of ultrasound. Piezoelectric transducers are utilized as the acoustical energy sources. The transducers are formed so as to direct the acoustical waves to the prostate tissue and away from the rectal wall by creation of an acoustical "dead zone". The transducers are covered by a protective sheath and a water-coolant system is provided to control the catheter temperature.

U.S. Pat. No. 6,066,139 describes the use of ultrasound to generate lesions in a fallopian tube without surgical exposure of the tube. The lesions are then allowed to heal naturally, forming fibrous growths which seal the tubes. Transducers of the device disclosed in this patent are covered by a sealant, and a coolant is supplied for temperature control. Temperature measurement is performed with thermal sensors affixed to a catheter.

The devices disclosed in the references cited above present a number of undesirable features. For example, the sealants or sheaths around piezoelectric transducers absorb and attenuate the acoustical waves that would otherwise reach the tissues, as well as adding bulk and increasing the size of the devices. Absorption of the acoustical energy causes the sealants or sheaths to self-heat, causing the affected tissue to desiccate too rapidly or become charred, thereby increasing the risk of excessive tissue damage. The provision of a coolant system for the probe can reduce this risk, but it increases the overall diameter of the probe, making the probe less flexible, and it increases the complexity of the treatment device.

There remains a need to develop a reliable method for sterilization to prevent pregnancy, preferably one that reduces the need for surgery or other invasive techniques to observe the extent of coagulation and allows the controlled application of energy to the tissue without attenuation or the need for coolants. It is also preferable that the method allow the thermal energy source to be placed accurately within the fallopian tube without relying on invasive visualization techniques.

SUMMARY OF THE INVENTION

One aspect of the invention includes an apparatus for sterilizing a female patient in a transcervical procedure, comprising an elongated catheter with a piezoelectric ultrasound transducer at its distal end. The apparatus is arranged for creating a thermal lesion in a fallopian tube through acoustical heating of the tissue. In a preferred embodiment of the apparatus, the transducer is cylindrical in shape and sized to be inserted into a fallopian tube with the outer surface of the cylinder in direct contact with the surrounding tissue. A source of radiofrequency (RF) current is provided for energizing the transducer, thereby generating a radially dispersing acoustical wave front that can be applied directly to the surrounding tissue. In another preferred embodiment, the apparatus includes a thermal sensor that can be moved independently of the catheter to measure the tissue temperature at multiple locations along the lesion. Another preferred embodiment provides a conical, helical spring attached to the catheter for centering the distal end of the catheter in the opening of a fallopian tube and guiding insertion of the transducer. The spring also provides a tactile means for determining that the spring and transducer have been correctly positioned in the uterus for the sterilization procedure.

Another aspect of the invention includes transcervical procedures for performing sterilization of a female patient using acoustical heating by ultrasound transmission. In a preferred procedure, the distal end of a catheter with an attached cylindrically shaped ultrasound transducer is introduced into the uterus transcervically and guided to the opening of a fallopian tube. The transducer is inserted into the intramural region of the fallopian tube with the outer surface of the transducer in direct contact with the tissue of the fallopian tube. A radiofrequency (RF) current is applied to the transducer, causing it to generate a radially dispersing acoustical wave front that heats the adjacent tissue, thereby forming a thermal lesion around the circumference of the transducer. Another preferred procedure includes the step of positioning a thermal sensor at two or more different positions along the distal end of the catheter to monitor the changes in temperature as the lesion forms. The RF current may be intermittently interrupted or the power adjusted in response to a signal from the thermal sensors so as to control the tissue temperature.

The apparatus and method provide a minimally invasive means for performing a sterilization through a controlled application of energy to the tissue of the fallopian tube. As the surface of the lesion heals, a fibrous tissue forms that reliably closes off the fallopian tube. The absence of a sheath or sealant around the piezoelectric transducer keeps the diameter of the transducer small enough for convenient insertion and reduces the potential for attenuation of the acoustic wave front or self-heating of the apparatus.

BRIEF DESCRIPTION OF THE DRAWINGS

For a more complete understanding of the present invention, reference is made to the following detailed description of the present invention considered in conjunction with the accompanying drawings, in which.

DETAILED DESCRIPTION OF THE INVENTION

Figure 1:
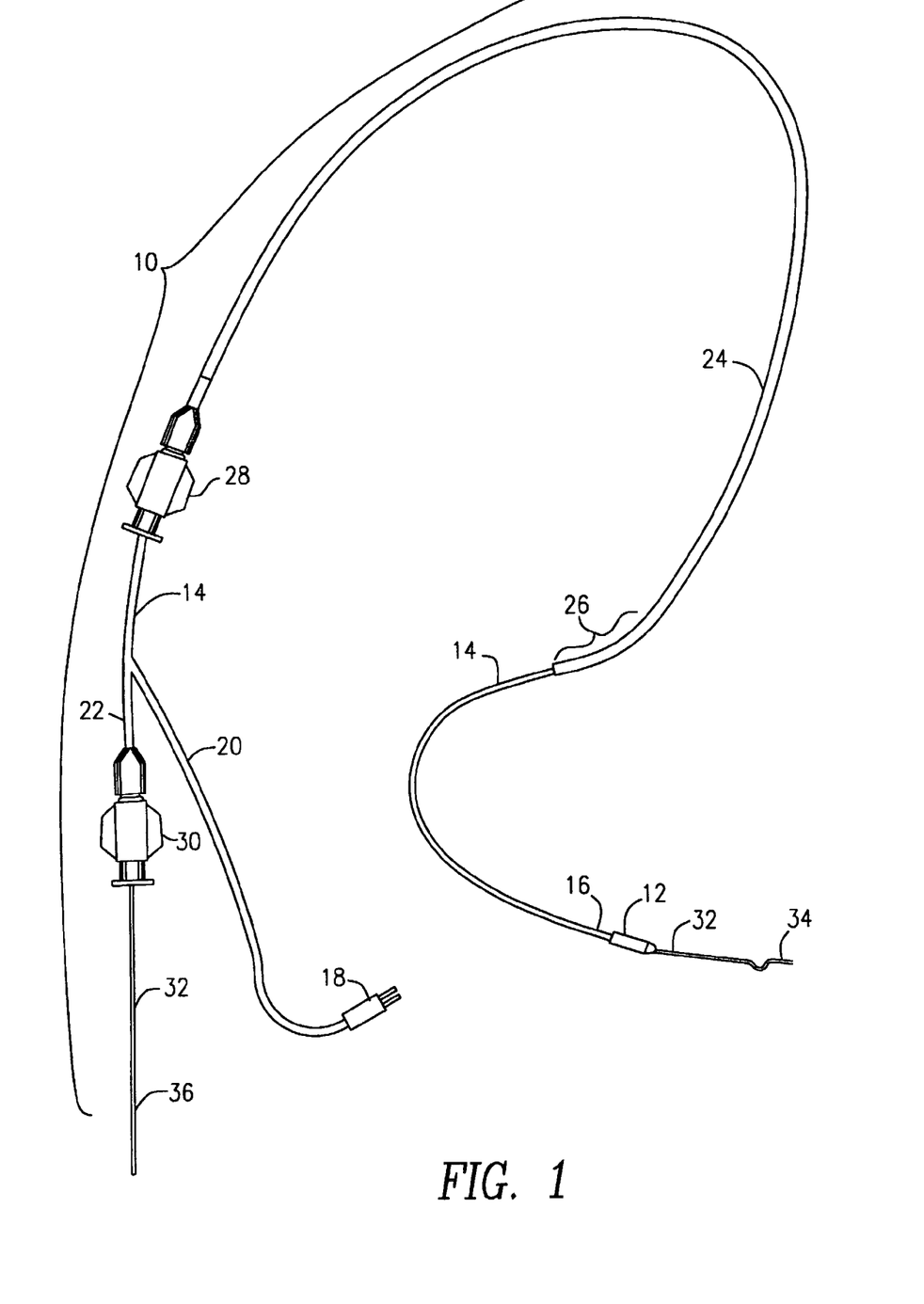
FIG. 1 is a top plan view of a transcervical sterilization apparatus constructed in accordance with the present invention.

FIG. 1 illustrates a sterilization apparatus 10 constructed in accordance with the present invention. More particularly, the apparatus has a piezoelectric transducer 12 for performing transcervical sterilization. A flexible catheter 14, which has distal and proximal ends 16, 18, carries the piezoelectric transducer 12 on the distal end 16. The catheter 14 is generally circular in cross-section and is sized and shaped for transcervical insertion into a fallopian tube. The catheter 14 is provided with a branch 20 that terminates in a connector 22 for electrically connecting the apparatus 10 to a power generator, a signal conditioner or other electronic circuitry used in a transcervical sterilization procedure (see FIG. 8). Alternatively, the connector 22 can be integrated into the proximal end 18 of the catheter 14.

An inserter 24 (see FIG. 1) is provided so as to facilitate insertion of the catheter 14 through a cervix and into a fallopian tube. More particularly, the catheter 14 is movably mounted in the inserter 24 such that it is extendable and retractable through the inserter 24. The inserter 24 is flexible and is, preferably, provided with a preformed bend 26 to guide the catheter 14 in a proper direction within a uterus.

The apparatus 10 is also provided with conventional mechanisms to manipulate the catheter 14, such as handles 28, 30 illustrated in FIG. 1.

The apparatus 10 is also provided with a flexible guide wire 32 that extends through the length of the catheter 14. The guide wire 32 has a distal end 34 adapted for insertion into a fallopian tube and hence made so as to be softer and more flexible than the main body of the guide wire 32. The guide wire 32 also has a proximal end 36 that is straight and substantially stiff such that it is suitable for use in manipulating the guide wire 32. As is conventional in the catheter field, the proximal end 36 can be provided with calibrated markings (not shown) indicating a distance traveled by the guide wire 32.

Figure 2:
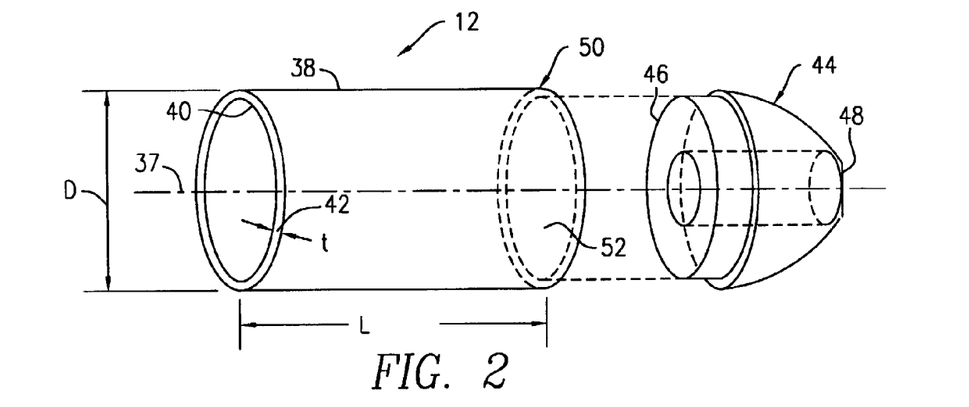
FIG. 2 is an exploded perspective view of a piezoelectric transducer assembly of the apparatus shown in FIG. 1.

With reference to FIGS. 1 and 2, the piezoelectric transducer 12 is adapted to function as an energy source for creating a thermal lesion within a fallopian tube. When energized by a radiofrequency (RF) current, the transducer 12 generates an acoustical wave that is absorbed by a surrounding tissue and converted into heat. Because the acoustical energy radiates as a collimated wave front in a direction perpendicular to the surface of a transducer, the transducer 12 is provided with a cylindrical shape for causing the wave front to be directed radially outwardly from the central axis 37 of the transducer 12 toward tissue around the entire surface of the transducer 12. The transducer 12 and its surrounding tissue are acoustically coupled by direct contact between the transducer 12 and the tissue. Energy emitted from the transducer 12 is easier to control than energy emitted from bipolar or monopolar RF devices known in the prior art, as the extent of the affected tissue does not depend on the placement of an antipolar electrode or ground plate or on tissue electrical properties that vary with tissue desiccation.

Referring to FIG. 2, the transducer 12 is constructed as a thin cylinder made of a ceramic material (e.g., ceramic materials sold under part nos. PZT4, PZT8 or C5800 by ValpeyFischer Corp., Hopkinton, Mass.). An outer surface 38 and an inner surface 40 of the transducer 12 are coated with thin layers of conductive metal, e.g., nickel, gold or platinum, so as to form conductive coatings 39, 41 (see FIG. 3) along the entire outer and inner surfaces 38, 40 respectively. The conductive coatings 39, 41 may be formed by vapor deposition or other methods known in the art and are deposited so that the conductive coating 39 of the outer surface 38 does not come in contact with, and is hence electrically insulated from, the conductive coating 41 of the inner surface 40.

Still referring to FIG. 2, the transducer 12 is sized to fit within a fallopian tube and to directly come in contact with a sufficient length of tissue so that the fallopian tube can be sealed when the lesioned tissue heals. For instance, transducer 12 can be provided with an outer diameter D of 1–2 mm, preferably the same outer diameter as catheter 14, and a length L of 5–10 mm.

The transducer 12 is also provided with a tapered tip 44 (see FIG. 2) to minimize tissue damage and to facilitate the entry of the transducer 12 into a fallopian tube. The tip 44 is constructed as a separate piece of electrically insulating material for attachment to a distal end 50 of the transducer 12. The separately-formed tip 44 is provided with a protruding plug 46 that fits into a hollow interior 52 of the transducer 12 and functions to align the tip 44 with respect to the transducer 12. An axial passage 48 extends through the tip 44 to accommodate passage of the guide wire 32 therethrough. Alternatively, the tip 44 may be formed integrally with the distal end 50 of the transducer 12. In such circumstances, the tip 44 can be electrically insulated from the surfaces 38, 40 of the transducer 12 to prevent the tip 44 from being energized. In the absence of a tapered tip 44, the transducer 12 may simply be plugged at its distal end 50.

Figure 3:
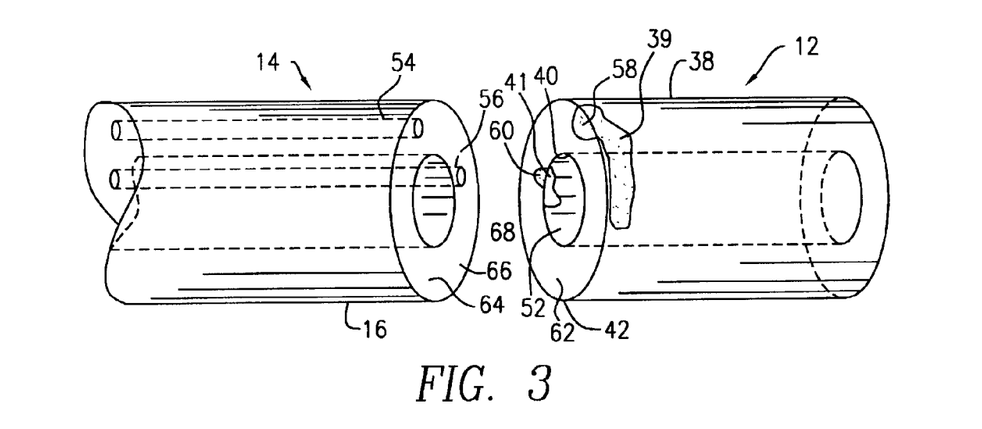
FIG. 3 is an exploded perspective view of an arrangement for electrically connecting the transducer assembly shown in FIG. 2 to an end of a catheter.

Now-referring to FIG. 3, the transducer 12 is adapted to be energized by an RF current supplied through a bipolar pair of conductive leads 54, 56 which extend through the catheter 14 and terminate at the connector 22. Other arrangements for carrying and terminating the conductive leads 54, 56 will be obvious to ordinarily-skilled practitioners in the field of medical instrumentation. An RF current is supplied to the transducer 12 at the resonant frequency of the transducer 12 which is proportional to the thickness t (see FIG. 2) of a wall 42 of the transducer 12. Typically, the resonant frequency of the transducer 12 is between 6–12 MHz and, preferably, is about 10 MHz.

Still referring to FIG. 3, the leads 54, 56 are electrically connected to the conductive coatings 39, 41, respectively, of the surfaces 38, 40, respectively, of the transducer 12. The electrical connection between the outer conductive coating 39 and the conductive lead 54 is preferably formed so that it does not increase the outer diameter D of the transducer 12. In this regard, the transducer 12 is coupled to the catheter 14 in an end-to-end manner such that the catheter 14 can be provided with the same outer diameter as the transducer 12. The thicknesses of the wall 42 of the transducer 12 and a wall 64 of the catheter 14 are exaggerated in FIG. 3 for the sake of clarity. The transducer wall 42 terminates in an end face 62 which, preferably, is substantially flat and perpendicular to the axis 37 of the transducer 12. The conductive coating 39 of the outer surface 38 extends onto the end face 62, forming a conductive area 58. The conductive coating 41 of the inner surface 40 also extends onto the end face 62, forming a conductive area 60 which is separated and hence electrically isolated from the conductive area 58 and the outer surface 38. The distal end 16 of the catheter 14 terminates in an end face 66 which, preferably, is sized and shaped to fit against the end face 62 of the transducer 12. The conductive leads 54, 56 are exposed at the end face 66. The end face 62 of the transducer 12 is attached to the end face 66 of the catheter 14 so that the lead 54 makes contact with the conductive area 58 and the lead 56 makes contact with the conductive area 60. The end faces 62, 66 are secured to each other, preferably, by an adhesive layer provided between the end faces 62, 66. The conductive leads 54, 56 are preferably embedded within the catheter wall 64 so as to minimize the risk of damage to the leads 54, 56 during fabrication and use of the assembly 10. Alternatively, the conductive leads 54, 56 can be routed through a lumen 68 of the catheter 14. Conductive leads 54, 56 may also be arranged in a co-axial fashion with conductive lead 54 being the inner conductor and conductive lead 56 being the outer conductor. The conductive areas 58, 60 would be arranged to make electrical contact with the conductive leads 54, 56, respectively.

The transducer 12 is not provided with a sealant or other covering. Rather, the transducer 12 remains exposed so that it may come in direct contact with tissue of a fallopian tube along the entire outer coating 39 of the transducer 12. Such contact allows an acoustical wave generated by the energized transducer 12 to be transmitted to the tissue without absorption or attenuation by an intervening material. The absence of a sealant or other covering also keeps the diameter of the transducer 12 small, so that the transducer 12 fits more readily into the entrance of the fallopian tube.

Figure 5:
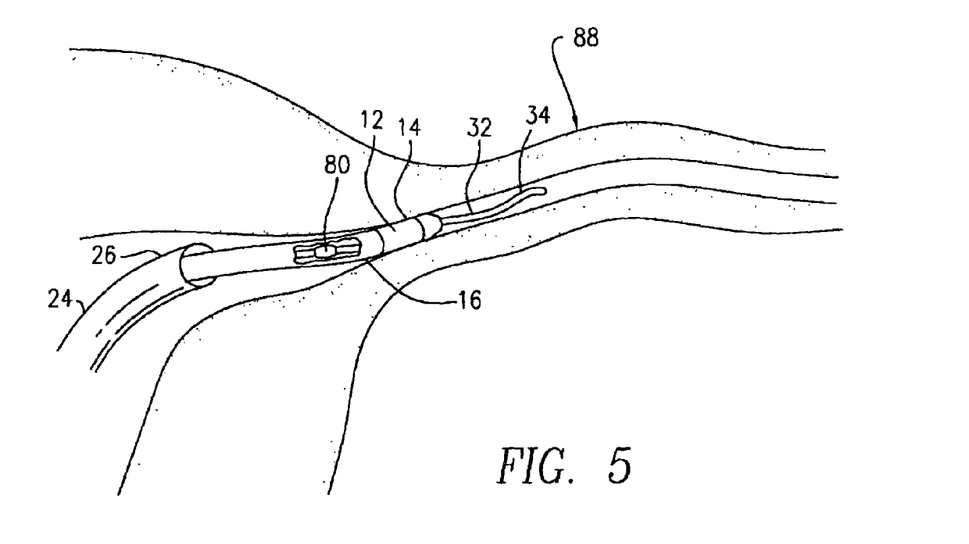
FIG. 5 is a partially cutaway view of the apparatus shown in FIG. 1 with its distal end inserted into a fallopian tube for sterilization showing a thermal sensor in its retracted position.
Figure 6:
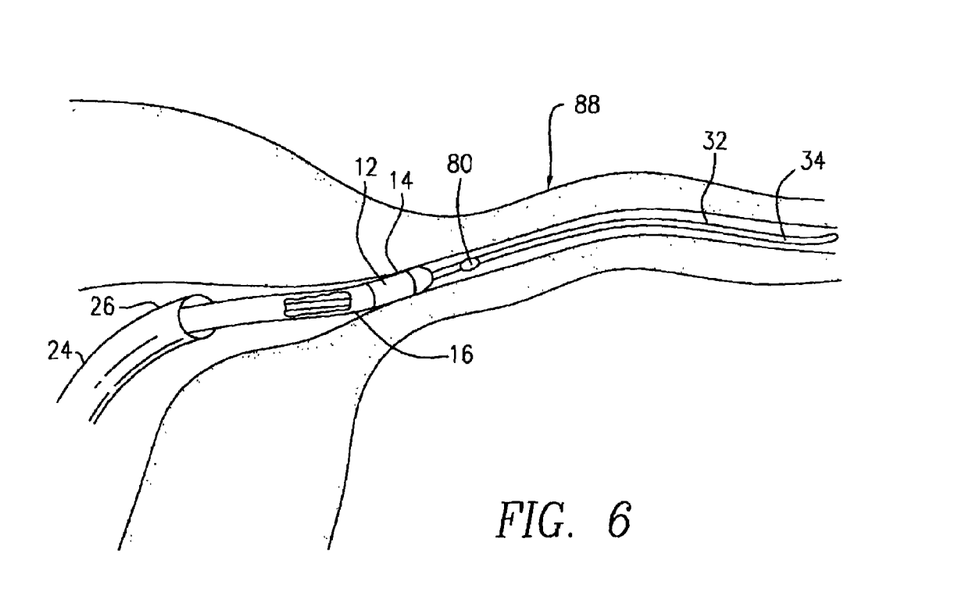
FIG. 6 is a view similar to FIG. 5, except that the thermal sensor is shown in its extended position.

With reference to FIG. 5, a thermal sensor 80 is provided to monitor the temperature of the transducer 12 and the adjacent tissue of a fallopian tube. The thermal sensor 80 is preferably placed on an exterior surface of the guide wire 32 or embedded within the guide wire 32 adjacent the distal end 34 thereof so that the thermal sensor 80 can be positioned to monitor the temperature at various locations relative to the transducer 12 during a sterilization procedure. For example, the thermal sensor 80 may be initially positioned in its retracted position (see FIG. 5), in which it is placed within the catheter 14 near the transducer 12, and then moved through the transducer 12 to its extended position (see FIG. 6), in which it is located outwardly beyond the taper tip 44 (i.e., it is located outside of the apparatus 10). The temperature profile obtained by measuring temperatures at various locations between the retracted and extended positions of the thermal sensor 80 may be used to determine the length of the tissue subjected to heating. Because of their small diameters and direct contact with the surrounding tissue, both transducer 12 and the adjacent regions of the catheter 14 rapidly reach thermal equilibrium with the tissue, allowing accurate measurement of the temperature of the tissue from within the transducer 12 or the catheter 14. The thermal sensor 80 is also adapted to provide a rapid response to temperature differences as it is moved between locations. The thermal sensor 80 may be a thermistor or thermocouple, or a sensor or probe used in other measurement techniques such as fiber optic measurement of phosphorescent decay times. In other embodiments, the thermal sensor 80 may be fixedly mounted to another element of the apparatus 10, such as within the lumen 68 or wall 64 of the catheter 14, on the inner surface 40 of the transducer 12 or within the tapered tip 44. The thermal sensor 80 is provided with a signal lead (not shown) for transmitting an analog signal from the thermal sensor 80 to terminals at the connector 22 or the apparatus 10.

Figure 8:
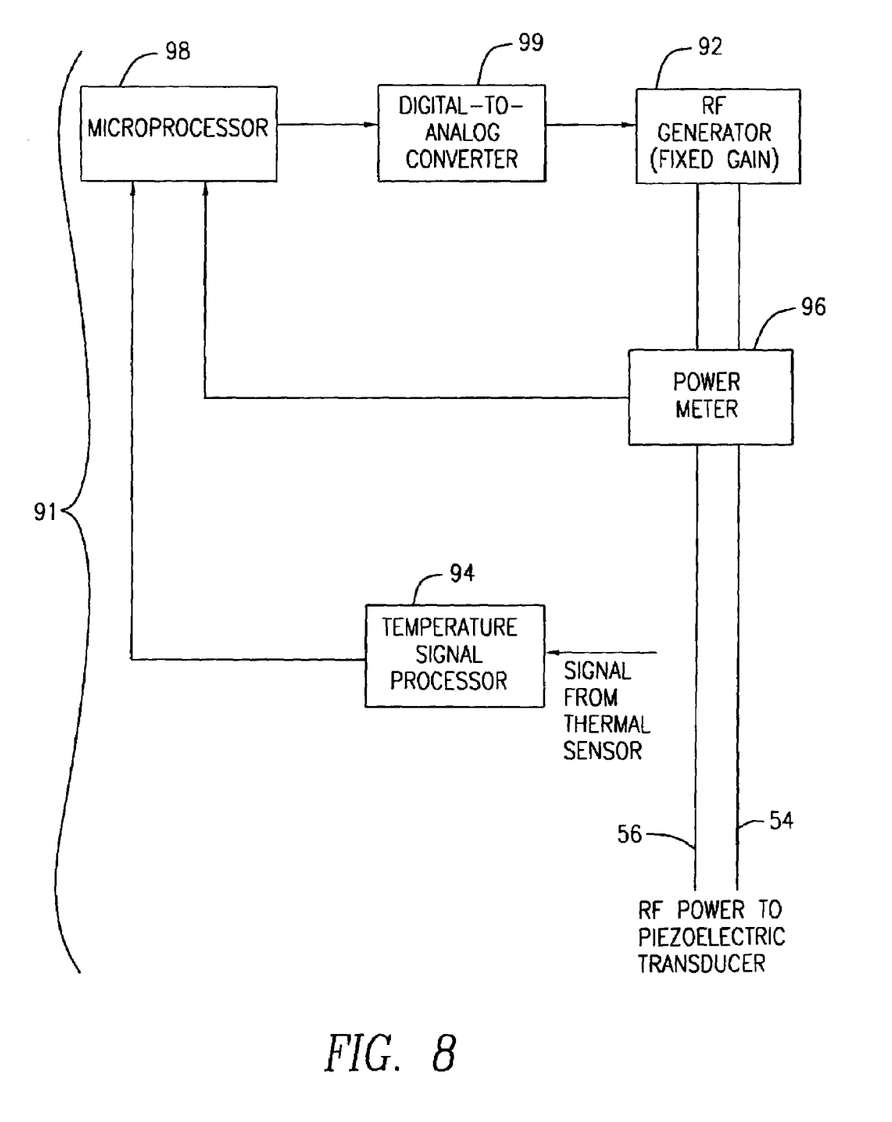
FIG. 8 is a schematic diagram of electronic power control unit for controlling a supply of RF current to the apparatus shown in FIG. 1.

Referring to FIG. 8, a power control unit 91 is provided to supply RF power to the transducer 12 through connector 22 and conductive leads 54, 56. The power control unit 91 includes an RF generator 92 operating at fixed gain, a temperature signal processor 94 for converting the analog signal received from the thermal sensor 80 to a digital data signal, a power meter 96 for monitoring the power supplied to and returned from the transducer 12 and converting the measured power values to a digital data signal, and a microprocessor 98 for controlling the operation of the RF generator 92 in response to digital data signals received from the temperature signal processor 94 and the power meter 96.

In order to perform transcervical sterilization using the apparatus 10, conventional preparation procedures (e.g., local or general anesthesia) are performed to prepare the patient. The catheter 14 is then inserted through a cervix 82 (see FIG. 7) and advanced toward a fundus 84 in a conventional manner. More particularly, the catheter 14 is advanced by a sequence of predetermined distances until it extends through an entrance 86 of a fallopian tube 88 by a distance sufficient such that the transducer 12 is placed approximately 1–2 cm into the fallopian tube 88, but within the uterus. Placement of the catheter 14 is facilitated by the preformed bend 26 of the inserter 24, which functions to direct the catheter 14 toward the entrance 86. The guide wire 32 may also be used to position the catheter 14 by advancing the guide wire 32 into the entrance 86 and then moving the catheter 14 over the guide wire 32. During the insertion process, the position of the catheter 14 relative to the entrance 86 may be viewed with the use of an invasive method (e.g., using a fiber optic probe carried by the catheter 14) or an echogenic ultrasound technique, such as sonography, or by using the transducer 12 as an ultrasound source detectable by external sensors.

After the transducer 12 is properly positioned in the fallopian tube 88, a fixed level of RF current is supplied to the transducer 12 by the RF generator 92 (see FIG. 8) through the leads 54, 56. The rate of power delivery and the rate of return, or reflected, power are monitored continuously by power meter 96 in a conventional manner. Power is delivered to the transducer 12 at the resonant frequency of the transducer 12 which may be determined in a conventional manner (e.g., by tuning the frequency of the delivered current to obtain the maximum transmission of acoustical energy).

Figure 7:
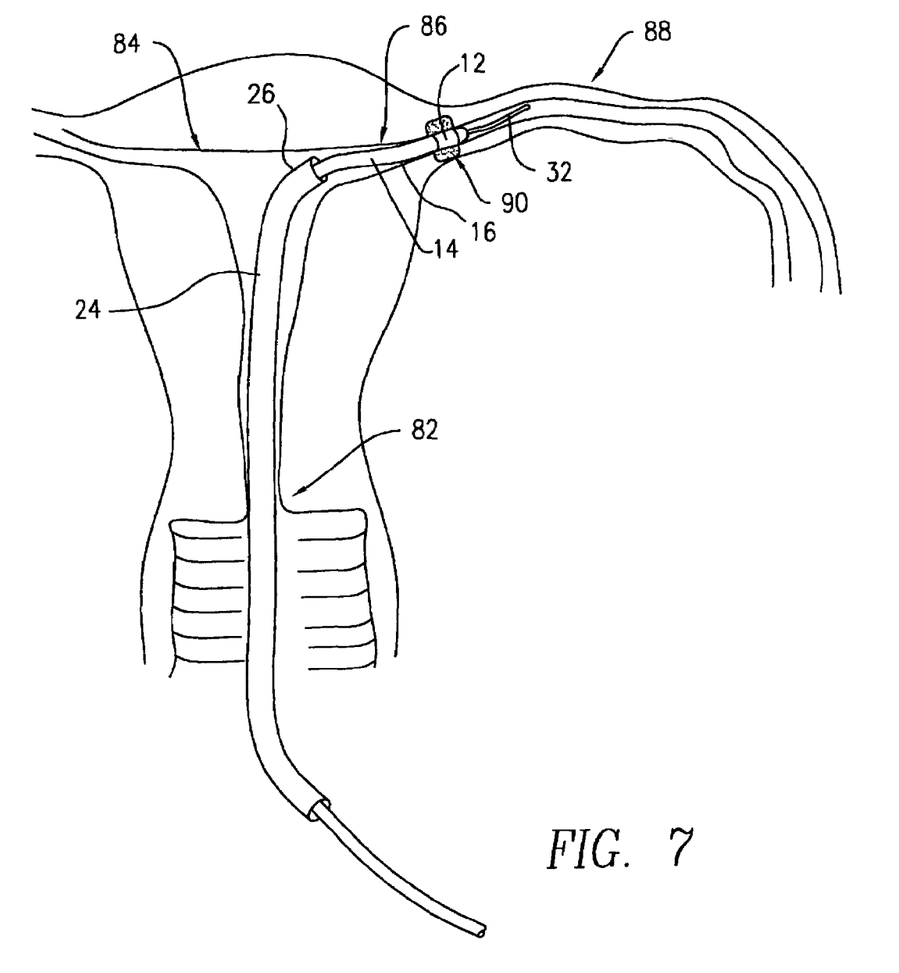
FIG. 7 is a schematic view of the apparatus shown in FIG. 1 as deployed during a sterilization procedure.

When energized by the RF current supplied from the RF generator 92, the transducer 12 generates an acoustical wave that radiates as a radially dispersing, collimated wave front from the outer surface 38 of the transducer 12 to the surrounding tissue of the fallopian tube 88. The acoustical energy is absorbed by the tissue and transformed into heat, thereby raising the temperature of the tissue. By this process, known as acoustical heating, the temperature of the tissue is increased until a lesion 90 is formed in the tissue surrounding the transducer 12. The level and rate of energy application is monitored and controlled to prevent excessive damage to the tissue of the fallopian tube 88. Tissue that is heated too rapidly or maintained at temperatures above a preferred range of 95° C.–105° C. may desiccate too quickly or char excessively. Either of these conditions may inhibit the natural collapse of the fallopian tube 88 when the catheter 14 is removed and interfere with the subsequent closure of the fallopian tube 88 as the lesion 90 is healed. Rapid or excessive heating may also cause steam and pressure waves in the narrow confines of the fallopian tube, which can result in perforation of tube wall or other damage.

The progression of the thermal lesion 90 is controlled by limiting the rate of temperature rise in the surrounding tissue and maintaining the temperature of the tissue near the midpoint of the preferred temperature range of 95° C.–105° C. Tissue temperature is continuously monitored with the use of the thermal sensor 80, which may be moved along the axis of catheter 14 by moving the guide wire 32 to create a temperature profile of the affected tissues. The temperature signal processor 92 processes an analog temperature signal received from the thermal sensor 80 to eliminate RF interference and then converts the same to digital temperature data for interpretation by the microprocessor 98. The microprocessor 98 regulates the temperature rise and tissue temperature by sending analog control signals to the RF generator 92 to intermittently interrupt power transmission to the transducer 12, effectively turning the transducer 12 on and off for short intervals. Alternatively, the level of power delivered to the transducer 12 may be controlled by adjusting the current or voltage. To achieve such control, the microprocessor 98 provides the digital-to-analog converter 99 digital data describing the power level and frequency. The convertor 99 forms an analog signal (i.e., a sine wave of the required amplitude) and transmits the analog signal to the RF generator 92 which, in turn, adjusts the rate or frequency of the supplied power. The power meter 96 monitors the forward and reflected power levels and transmits the corresponding data to microprocessor 98 sends signals to microprocessor 98 to adjust the supplied power until the targeted levels are achieved. This process is mediated by the microprocessor 98 according to known methods.

The formation of the lesion 90 may also be monitored by changes in reflected power from the transducer 12. As the tissue of the fallopian tube 88 surrounding the transducer 12 becomes desiccated, its acoustical properties change, and absorption of the acoustical energy by the desiccated tissue becomes less efficient, typically being reduced by 10–40%. As the tissue desiccates, a mismatch may occur between the transducer 12 and the tissue, resulting in a higher reflected power measured at the power meter 96. The forward and reflected power levels are monitored by the power meter 96 which transmits digital data relating to the changes in power to the microprocessor 98. Changes in the acoustical properties of the lesioned tissue also affect the transmission of acoustical energy through the lesion 90, allowing the formation of the lesion 90 to be monitored by ultrasound detectors positioned outside of the patient's body. Invasive monitoring methods, such as transmission of visual images through fiber optic probes carried on the catheter 14 that function may also be used to observe blanching of the tissue as it becomes desiccated. Such fiber optic probes, used, e.g., in visualizing scopes, transmit light to illuminate the area of the affected tissue and return video images for viewing. Other phenomena related to lesion formation, such as charring of tissue or formation of steam or smoke, may also be observed by invasive monitoring methods.

After the lesion 90 has been properly formed, the catheter 14 is withdrawn from the fallopian tube 88 and then removed from the uterus through the cervix 82. The fallopian tube 88, which normally is a closed structure, collapses upon itself in the area of the lesion 90 and undergoes an immediate inflammatory response. Over a period of 3–10 days, fibrous growth of the damaged tissue causes the surfaces of the lesion 90 to adhere to each other, thereby closing the fallopian tube 88 and hence completing the sterilization of a female patent.

Figures 9, 10, 13:
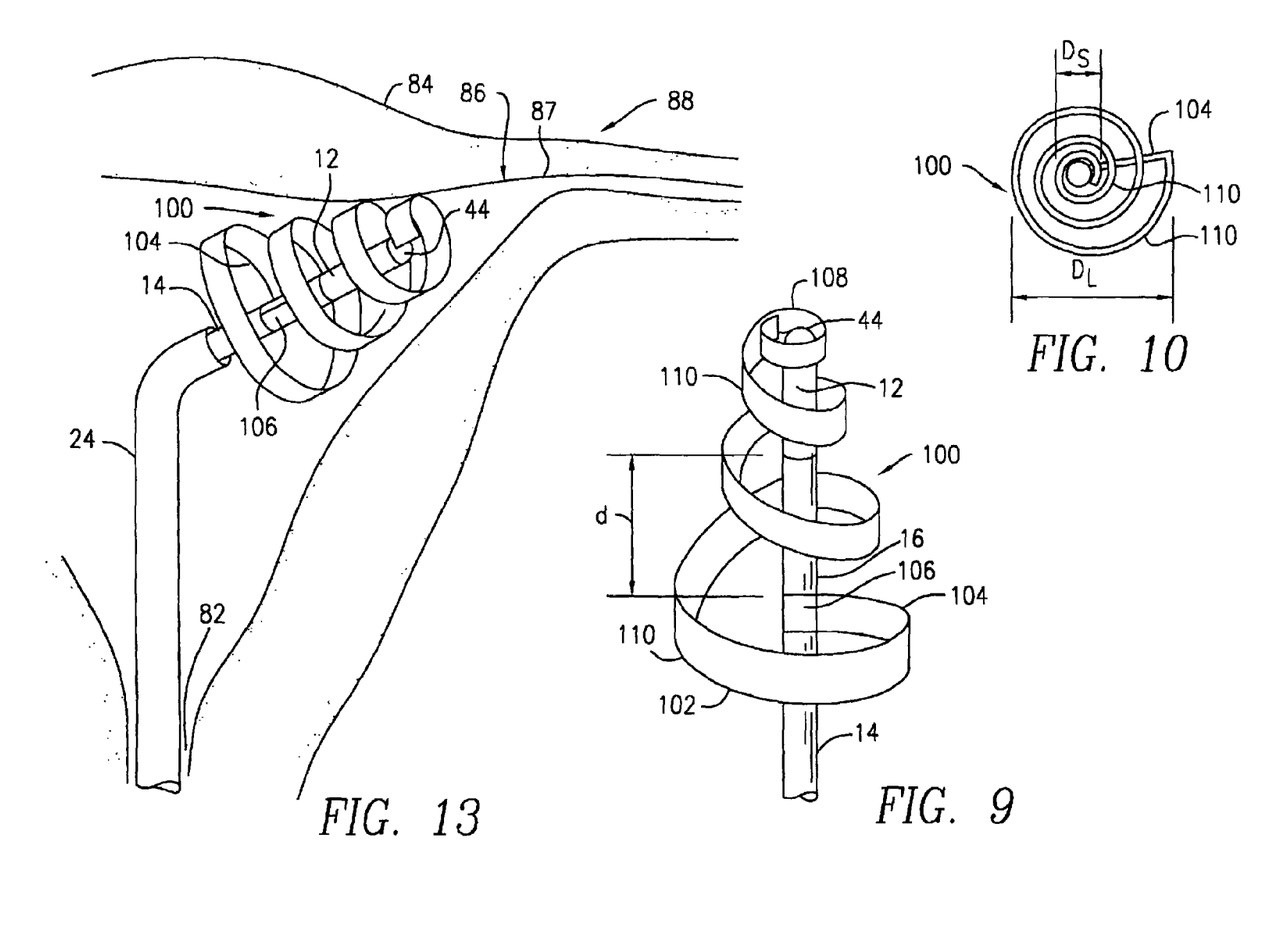
FIG. 9 is a perspective view of a centering device of the apparatus shown in FIG. 1.
FIG. 10 is a top view of the centering device shown in FIG. 9.
FIG. 13 is a perspective view of the centering device of FIG. 9 deployed in the body of a patient prior to the insertion of the transducer assembly into a fallopian tube.

FIGS. 9 and 10 illustrate a centering spring 100 adapted for use in aligning the distal end 16 of the catheter 14 with an intramural region 87 of the fallopian tube 88 during the deployment of the transducer 12 into the fallopian tube 88. For illustrative purposes, the diameters of the spring 100, the catheter 14 and the transducer 12 are exaggerated in FIGS. 9 and 10 in relation to their respective lengths. The spring 100 is made preferably from a resilient ("elastic") material, i.e., a material that returns to its original unstressed shape after being stretched, bent or compressed. While many different types of plastics or metal alloys can be used, a shape-memory alloy having optimal resilient ("superelastic") properties at about 37° C., i.e, near human body temperature (e.g., the nickel-titanium alloy known as nitinol) is particularly suitable for use in connection with the spring 100. In its relaxed or unstressed state (see FIG. 9), the spring 100 assumes the shape of a conical helix. The spring 100 is supported at its large-diameter end 102 by a support arm 104, which has an end 106 affixed to the distal end 16 of the catheter 14 such that it is located axially inwardly from the transducer 12. The connection between the affixed end 106 and the catheter 14 is sufficiently strong to withstand shear stresses resulting from the axial or radial compression of the spring 100. In this regard, the end 106 can be affixed to the catheter 14 by adhesive, solder, mechanical means (e.g., a retaining ring), or other suitable mechanisms. Preferably, the support arm 104 is formed integrally with the spring 100. The spring 100 is constructed from a ribbon of material and is hence provided with a rectangular cross-section. Alternatively, other shapes may be employed. For example, the spring 100 may be made from a wire-having a circular or square cross-section.

With reference to FIG. 9, in its relaxed or unstressed state, the spring 100 assumes a conical, helical shape such that it encompasses (i.e., spirals around) the catheter 14 and the transducer 12 and such that a small-diameter end 108 of the spring 100 is located at or axially outward from the tapered tip 44 of the transducer 12. Preferably, the small-diameter end 108 is centered relative to the tapered tip 44. The affixed end 106 is located at a distance d (e.g., about 2 cm) from the transducer 12 in an axially inward direction such that when the support arm 104 is placed within the funnel-shaped entrance 86 of the fallopian tube 88, transducer 12 is positioned in the intramural region 87 of the fallopian tube 88. In its relaxed state, the spring 100 has sufficient resilience to prevent coils 110 of the spring 100 from overlapping each other (see FIG. 10). Moreover, the conical spring 100 preferably has a large-end diameter $D_L$ of 4–6 mm and a small-end diameter $D_S$ of at least 2 mm, large enough to encompass the catheter 14. The shape of the spring 12 is not limited to the circular shape in the end view of FIG. 10. For example, the spring 12 may have an oval shape, conforming to the flattened shape of the uterus.

The deployment and use of the spring 100 are illustrated in FIGS. 11–15. Initially, the spring 100 is compressed or oriented into its compressed state so as to fit within the inserter 24. For example, the spring 100 may be wrapped into a tight helical spiral in partially overlapping fashion around the distal end 16 of the catheter 14 (see FIG. 11). The spring 100 can also be wound into a flat spiral with the end 106 on the inside of the spiral and the end 108 on the outside of the spiral 100 (see FIG. 12). The spring 100 is maintained in its compressed state by the inserter 24 until it is deployed for use-during the performance of a sterilization operation.

Figure 11:
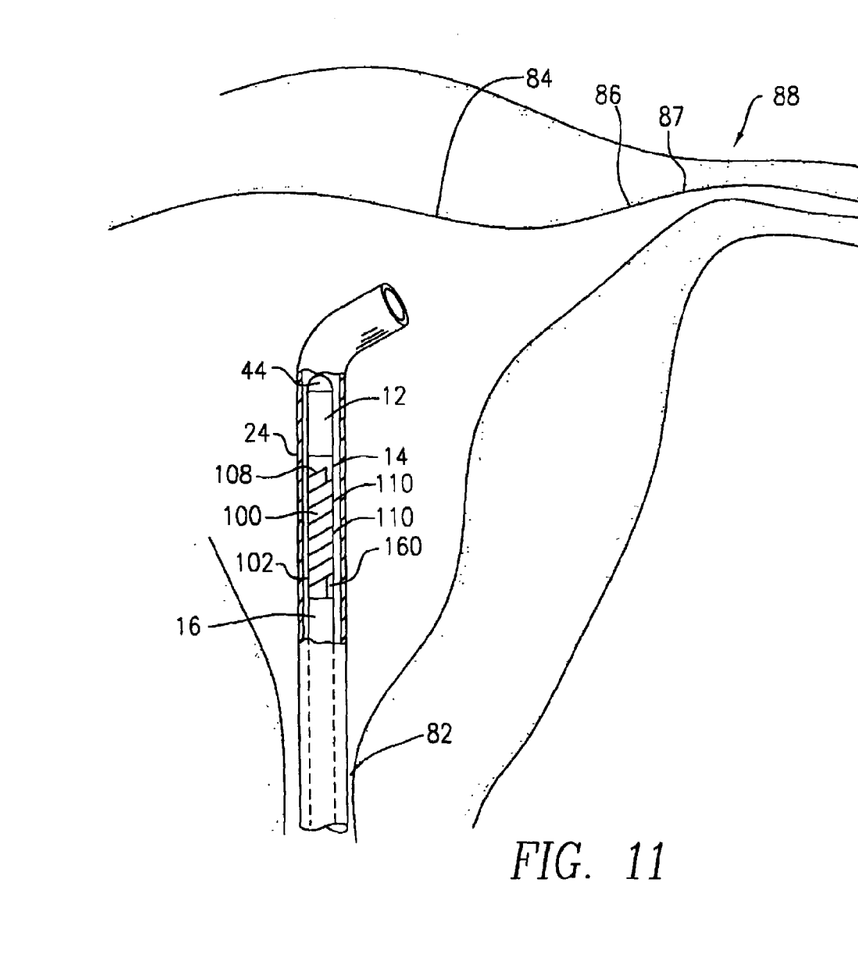
FIG. 11 is a partially cutaway view of a pre-deployment arrangement of the centering device shown in FIG. 9.
Figure 12:
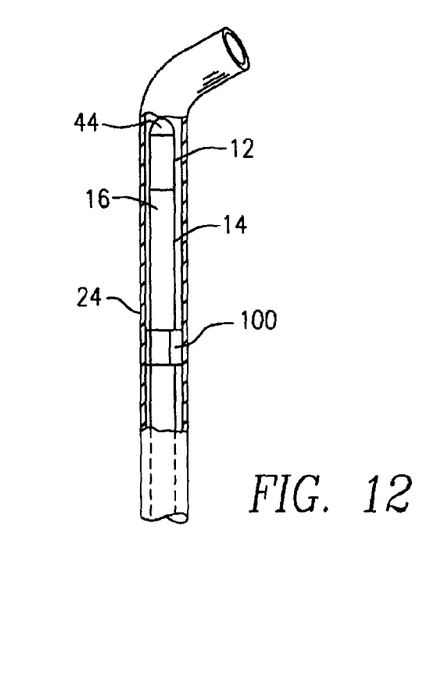
FIG. 12 is a partially cutaway view of another pre-deployment arrangement of the centering device shown in FIG. 9.
Figures 14, 15:
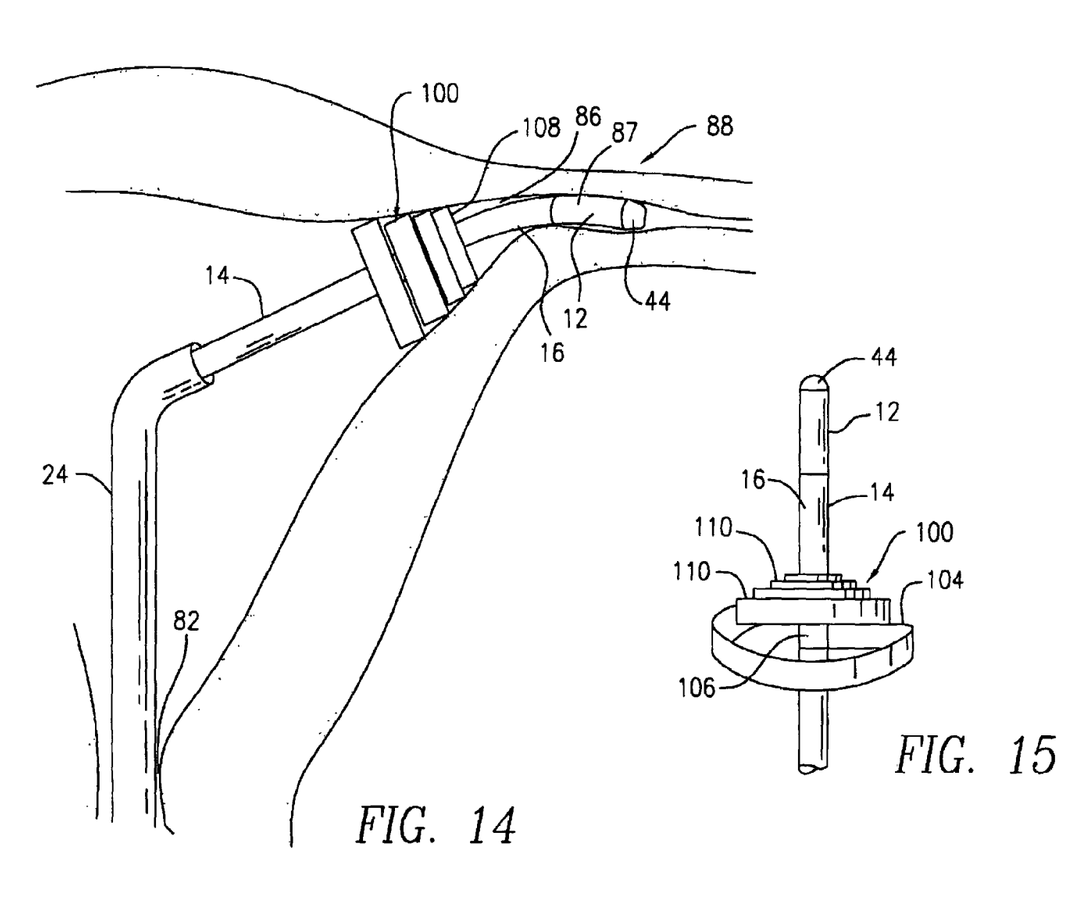
FIG. 14 is a view of the centering device of FIG. 9 in its partially compressed state during the insertion of the transducer assembly into the fallopian tube.
FIG. 15 is a side view of the centering device of FIG. 9 shown in its fully compressed state.

In use, with the spring housed within the inserter 24 (i.e., with the spring in its compressed state), the inserter 24 is passed through the cervix 82 and advanced toward the fundus 84 (see FIG. 11). The distal end 16 of the catheter 14 is then advanced out of the inserter 24, thereby releasing the spring 100 and hence allowing the same to assume its conical, helical shape (see FIG. 13). The catheter 14 is then manipulated until the spring 100 is properly positioned in the funnel-shaped entrance 86 of the intramural region 87. Because of the size and density of the spring 100, the position of the spring 100 can be readily confirmed by using an echoic ultrasound (sonograph) method. Because the spring 100 creates some mechanical resistance as it is compressed, an operator manipulating the catheter 14 can also manually feel that the spring 100 is seated at the entrance 86. As the catheter 14 is advanced further, the coils of the spring 100 press against the walls of the entrance 86, causing the spring 100 to collapse axially (see FIG. 14) and allowing the transducer 12 to extend beyond the small-diameter end 108. The spring 100 is constructed such that it resists radial compression, thereby causing the catheter 14 to remain centered relative to the spring 100. The catheter 14 is advanced until the transducer 12 is inserted into the fallopian tube 88. As shown in FIG. 15, the spring 100 may be compressed axially until its shape approaches that of a flat coil, at which point the support arm 104 blocks the further axial movement of coils 110. Attempts to advance the transducer 12 past this point create a much greater mechanical resistance as the support arm 104 engages the coils 110. When this resistance is detected, the operator may verify that the transducer 12 is in its desired position by a visualization method as discussed above. If necessary, the transducer 12 may be advanced further by applying sufficient axial force to deform the spring 100 so that the coils 110 are pushed over the support arm 104.

It should be appreciated that the present invention provides numerous advantages over the prior art discussed above. For example, the use of the piezoelectric transducer 12 as the energy source to create the thermal lesion allows better control of the extent of the lesion than use of the bipolar or monopolar RF devices known in the art. The transducer 12 transmits energy to the tissue independently of a return path, so electric current does not flow through the patient's body as in RF devices. The absence of a sealant or sheath around the transducer 12 allows transmission of acoustical energy to surrounding tissue without attenuation of the acoustical energy or self-heating of the apparatus 10. Moreover, the movable thermal sensor 80 is adapted for use in providing a temperature profile that may be used to delineate the extent of the lesioned tissue and assess the effectiveness of the thermal treatment. The centering spring 100 attached to the catheter 14 also provides advantages over the prior art, such as automatically centering the distal end 16 of the catheter 14 and hence the transducer 12 within the entrance to the fallopian tube and providing a tactile, non-visual means for the operator to estimate the position of the transducer within the fallopian tube itself.

Figure 4:
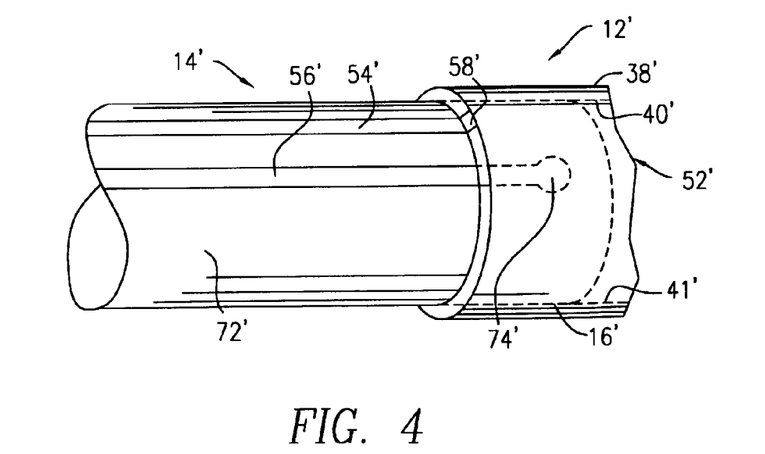
FIG. 4 is a perspective view of a modified version of the arrangement shown in FIG. 3.

It should be understood that variations and modifications can be made to the disclosed invention. For example, FIG. 4 illustrates a modified version of the electrical connection shown in FIG. 3 between the transducer 12 and the catheter 14. Conductive leads 54', 56' are mounted on an outer surface 72' of the catheter 14'. Preferably, the leads 54', 56' are formed from electrically conductive tapes attached to the outer surface 72'. The catheter 14' has a distal end 16' sized and shaped to fit into the hollow interior 52' of the transducer 12' such that the outer surface 72' of the catheter 14' is in contact with the inner surface 40' of the transducer 12'. The conductive lead 54' terminates at a conductive area 58' located on the transducer 12' such that the conductive area 58' is in contact with the electrically conductive coating of the outer surface 38' of the transducer 12'. The conductive lead 56' is provided with a terminal 74' located on the outer surface 72' at the distal end 16' such that the terminal 74' is located at the interface between the distal end 16' of the catheter 14' and the inner surface 40' of the transducer 12' so as to make electrical contact with the conductive coating of the inner surface 40'. An insulating layer (not shown) surrounding the leads 54', 56' and the outer surface 72' may be provided for protecting the leads 54', 56' during the handling and use of the apparatus 10. Another possible variation would be to use more than one piezoelectric transducer, spaced along the axis of the catheter 14. Each of the additional transducers can be mounted to the catheter 14 coaxially therewith and can preferably be provided with a separate pair of conductive leads, allowing the individual transducers to be controlled independently of each other. The additional transducers can have an axial length L that is substantially smaller than that of the transducer 12 and can be spaced sufficiently far apart from each other to avoid stiffening of the otherwise flexible catheter 14. In another variation, a movable thermal sensor and guide wire may be provided outside of the piezoelectric transducer, rather than through it.

Although the invention disclosed herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the invention as defined in the appended claims.

We claim:

1. Apparatus adapted for use in forming a thermal lesion in a fallopian tube of a patient, comprising a catheter having a distal end section, said distal section including generating means for generating an ultrasound acoustical wave front radiating therefrom, said generating means being sized and shaped so as to be inserted into a fallopian tube of a patient for forming a thermal lesion in the fallopian tube by the application of an ultrasound acoustical wave front generated by said generating means, said generating means including an outer surface such that, when said generating means is inserted into the fallopian tube, said outer surface comes in direct contact with a surrounding tissue of the fallopian tube, whereby the acoustical wave front can be applied directly to the surrounding tissue from said generating means; and a centering spring attached to said distal section of said catheter.

2. The apparatus of claim 1, wherein said spring is sized and shaped so as to be positioned in an entrance of an intramural region of the fallopian tube for facilitating the insertion of said generating means into the fallopian tube.

3. The apparatus of claim 2, wherein said spring is made from a resilient material such that it is compressible into a compressed condition and expandable into an expanded condition.

4. The apparatus of claim 3, wherein said resilient material is a shape-memory alloy.

5. The apparatus of claim 3, wherein said spring assumes a conical, helical shape when it is in said expanded condition.

6. The apparatus of claim 5, wherein said spring moves from said expanded condition to said compressed condition during the insertion of said generating means into the fallopian tube.

7. The apparatus of claim 6, wherein said spring in said compressed condition inhibits the insertion of said generating means further into the fallopian tube.

8. The apparatus of claim 6, wherein said spring is resilient such that it can be wrapped around said distal section of said catheter for transcervical insertion of said distal section of said catheter.

9. The apparatus of claim 8, comprising an inserter for placing said catheter transcervically in a uterus of the patient, said catheter being movably mounted through said inserter such that said distal section of said catheter is movable between a first position, in which it is positioned within said inserter, and a second position, in which it is positioned axially outwardly from said inserter.

10. The apparatus of claim 9, wherein said spring is wrapped around said distal section of said catheter and positioned in said inserter with said distal section of said catheter when said distal section of said catheter is positioned in said first position; and wherein said spring is in said expanded condition when said distal end of said catheter is positioned in said second position.

11. Apparatus adapted for use in forming a thermal lesion in a fallopian tube of a patient, comprising a catheter having a distal end section, said distal section including generating means for generating an ultrasound acoustical wave front radiating therefrom, said generating means being sized and shaped so as to be inserted into a fallopian tube of a patient for forming a thermal lesion in the fallopian tube by the application of an ultrasound acoustical wave front generated by said generating means; and a centering spring attached to said distal section of said catheter, said spring being sized and shaped so as to be positioned in an entrance of an intramural region of the fallopian tube for facilitating the insertion of said generating means into the fallopian tube.

12. A method for performing transcervical sterilization on a patient, comprising the steps of providing a catheter having a distal section which includes generating means, having an electrically conductive outer surface, said generating means for generating an ultrasound acoustical wave front, and a centering spring attached to said distal section, said centering spring being sized and shaped so as to be positioned in an entrance of an intramural region of a fallopian tube of a patient; positioning said centering spring in said entrance so as to facilitate inserting said generating means into said fallopian tube; inserting said generating means into a said fallopian tube such that said outer surface of said generating means directly contacts surrounding tissue of the patient's fallopian tube; and directly delivering the wave front to the surrounding tissue of the patient's fallopian tube by activating said generating means so as to form a thermal lesion in the tissue of the patient's fallopian tube.

13. The method of claim 12, wherein said positioning step includes the step of compressing said centering spring so as to create mechanical resistance to said inserting step.

14. The method of claim 12, wherein said catheter is provided with an inserter such that said distal section may be moved from a first position, in which said distal section is positioned within said inserter, and a second position, in which said distal section is positioned axially outwardly from said inserter, and wherein said centering spring is wrapped around said distal section within said inserter when said distal section is in its said first position and is in an expanded condition when said distal section is in its said second position, said method including the step of moving said distal section from said first position to said second position before the step of positioning said centering spring.

15. The method of claim 12, comprising the steps of providing a thermal sensor and positioning said thermal sensor adjacent to said distal section of said catheter.

16. The method of claim 15, wherein said step of positioning said thermal sensor includes the step of positioning said thermal sensor at at least two different positions relative to said distal section of said catheter so as to measure a temperature at each of said different positions.

17. The method of claim 16, wherein said activating step includes the steps of supplying a radiofrequency voltage to said generating means; and monitoring at least one analog signal transmitted from said thermal sensor.

18. The method of claim 17, comprising the steps of determining a temperature value and a rate of temperature change corresponding to said at least one analog signal; and intermittently interrupting the supply of said radiofrequency voltage to said generating means so as to control a temperature of said tissue surrounding said generating means.

19. The method of claim 18, wherein said step of intermittently interrupting the supply of said radiofrequency voltage to said generating means is performed so as to maintain said temperature of said tissue within a selected temperature range for a sufficiently long period of time so as to form a thermal lesion in said tissue of said fallopian tube.

20. The method of claim 19, wherein the selected temperature range is 95° C. to 105° C.

* * * * *